United States Patent
Murayama et al.

(10) Patent No.: US 9,056,189 B2
(45) Date of Patent: Jun. 16, 2015

(54) GUIDE WIRE

(71) Applicant: TERUMO KABUSHIKI KAISHA, Shibuya-ku (JP)

(72) Inventors: Hiraku Murayama, Fujinomiya (JP); Akihiko Umeno, Fujinomiya (JP); Jun Iwami, Fujinomiya (JP); Yutaka Itou, Fujinomiya (JP); Youki Aimi, Fujinomiya (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

(21) Appl. No.: 14/200,848

(22) Filed: Mar. 7, 2014

(65) Prior Publication Data

US 2014/0188083 A1 Jul. 3, 2014

Related U.S. Application Data

(60) Continuation of application No. 11/797,328, filed on May 2, 2007, now abandoned, which is a division of application No. 10/635,716, filed on Aug. 7, 2003, now abandoned.

(30) Foreign Application Priority Data

Aug. 8, 2002 (JP) .................................. 2002-232164
Dec. 6, 2002 (JP) .................................. 2002-355908
May 30, 2003 (JP) .................................. 2003-156011

(51) Int. Cl.
*A61M 25/09* (2006.01)
*B21F 15/08* (2006.01)

(52) U.S. Cl.
CPC .......... *A61M 25/09033* (2013.01); *A61M 25/09* (2013.01); *A61M 2025/09083* (2013.01); *A61M 2025/0915* (2013.01); *B21F 15/08* (2013.01)

(58) Field of Classification Search
CPC ................... A61M 25/09; A61M 2025/09083; B21F 15/08
USPC ......................................................... 600/585
See application file for complete search history.

(56) References Cited

U.S. PATENT DOCUMENTS 4,676,249 A 6/1987 Arenas et al.
4,854,330 A 8/1989 Evans, III et al.
(Continued)

FOREIGN PATENT DOCUMENTS

EP 0 806 220 A2 11/1997
JP 1-124473 A 5/1989
(Continued)

OTHER PUBLICATIONS

Final Notification of Reason for Refusal issued in corres. JP Patent Application No. 2003-156011 and English translation thereof, Dec. 18, 2007, JPO, 5 pages.*

(Continued)

*Primary Examiner* — Lee S Cohen
*Assistant Examiner* — Emily Lloyd
(74) *Attorney, Agent, or Firm* — Buchanan Ingersoll & Rooney PC

(57) ABSTRACT

A guide wire includes a first wire disposed on the distal side, and a second wire disposed on the proximal side and made from a material having an elastic modulus larger than that of the first wire. The first wire and the second wire are joined to each other by welding. The second wire has, in the vicinity of the welded portion, a small cross-sectional area portion having a cross-sectional area smaller than that of a proximal end portion of the first wire. The outer diameter of the small cross-sectional area portion is gradually reduced in the direction toward the distal end. The first wire and the second wire may be welded to each other by a butt resistance welding process. Since the change in rigidity of the guide wire becomes smooth in the longitudinal direction, the operationality and kink resistance of the guide wire are improved.

7 Claims, 7 Drawing Sheets

(56) References Cited

U.S. PATENT DOCUMENTS

| | | |
|---|---|---|
| 4,925,445 A | 5/1990 | Sakamoto et al. |
| 5,111,829 A | 5/1992 | Alvarez de Toledo |
| 5,171,383 A | 12/1992 | Sagaye et al. |
| 5,341,817 A | 8/1994 | Viera |
| 5,341,818 A | 8/1994 | Abrams et al. |
| 5,358,796 A | 10/1994 | Nakamura et al. |
| 5,365,943 A | 11/1994 | Jansen |
| 5,368,661 A | 11/1994 | Nakamura et al. |
| 5,372,144 A | 12/1994 | Mortier et al. |
| 5,409,015 A | 4/1995 | Palermo |
| 5,411,476 A | 5/1995 | Abrams et al. |
| 5,636,642 A | 6/1997 | Palermo |
| 5,637,089 A | 6/1997 | Abrams et al. |
| 5,695,111 A | 12/1997 | Nanis et al. |
| 5,701,911 A | 12/1997 | Sasamine et al. |
| 5,749,837 A | 5/1998 | Palermo et al. |
| 5,769,796 A | 6/1998 | Palermo et al. |
| 5,772,609 A | 6/1998 | Nguyen et al. |
| 6,001,068 A | 12/1999 | Uchino et al. |
| 6,019,737 A | 2/2000 | Murata |
| 6,039,700 A | 3/2000 | Sauter |
| 6,139,510 A | 10/2000 | Palermo |
| 6,165,292 A | 12/2000 | Abrams et al. |
| 6,196,964 B1 | 3/2001 | Loffler et al. |
| 6,203,485 B1 | 3/2001 | Urick |
| 6,210,312 B1 | 4/2001 | Nagy |
| 6,234,981 B1 | 5/2001 | Howland |
| 6,390,993 B1 | 5/2002 | Cornish et al. |
| 6,488,637 B1 | 12/2002 | Eder et al. |
| 6,492,037 B2 | 12/2002 | Shindo et al. |
| 6,692,841 B2 | 2/2004 | Shindo et al. |
| 6,918,882 B2 | 7/2005 | Skujins et al. |
| 7,892,187 B2 * | 2/2011 | Murayama et al. ............ 600/585 |
| 8,348,860 B2 * | 1/2013 | Murayama et al. ............ 600/585 |
| 2001/0011158 A1 | 8/2001 | Howland |
| 2001/0023319 A1 | 9/2001 | Miyata et al. |
| 2004/0030266 A1 | 2/2004 | Murayama et al. |
| 2014/0188084 A1 * | 7/2014 | Murayama et al. ............ 604/528 |

FOREIGN PATENT DOCUMENTS

| | | |
|---|---|---|
| JP | 04-009162 A | 1/1992 |
| JP | 04-292174 A | 10/1992 |
| JP | 06-047570 A | 2/1994 |
| JP | 06-063151 A | 3/1994 |
| JP | 8-004727 A | 1/1996 |
| JP | 8-019883 A | 1/1996 |
| JP | 08-084776 A | 4/1996 |
| JP | 10-033689 A | 2/1998 |
| JP | 10-057499 A | 3/1998 |
| JP | 10-118005 A | 5/1998 |
| JP | 10-179758 A | 7/1998 |
| JP | 10-328157 A | 12/1998 |
| JP | 11-000737 A | 1/1999 |
| JP | 11-057014 A | 3/1999 |
| JP | 11-057041 A | 3/1999 |
| JP | 11-151578 A | 6/1999 |
| JP | 11-176268 A | 7/1999 |
| JP | 2000-514326 A | 10/2000 |
| JP | 2002-078805 A | 3/2002 |
| JP | 2002-534167 A | 10/2002 |
| JP | 2003-159333 A | 6/2003 |
| WO | WO 98/01184 A1 | 1/1998 |
| WO | WO 00/40286 A1 | 7/2000 |
| WO | WO 01/36034 A2 | 5/2001 |
| WO | WO 03/030982 A2 | 4/2003 |
| WO | WO 03/057273 A2 | 7/2003 |

OTHER PUBLICATIONS

European Search Report for EP 03017952, Dec. 9, 2003, EPO, 4 pages.*

* cited by examiner

F I G. 2 A
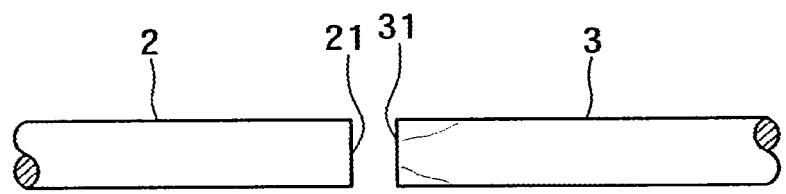
F I G. 2 B
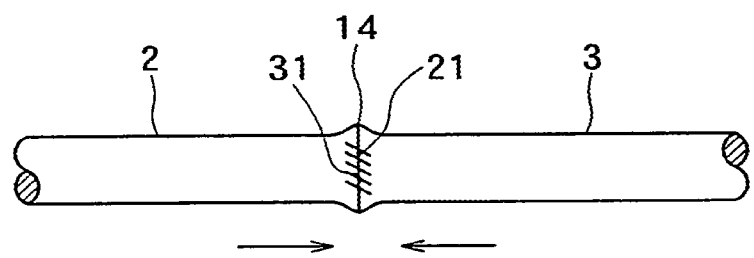
F I G. 2 C
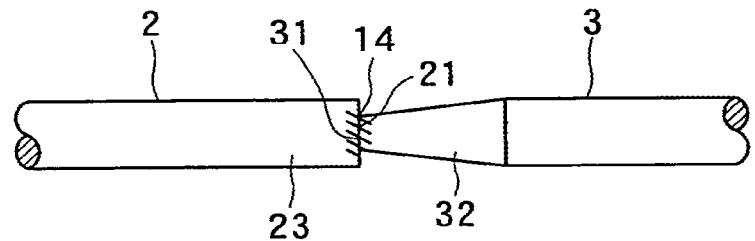

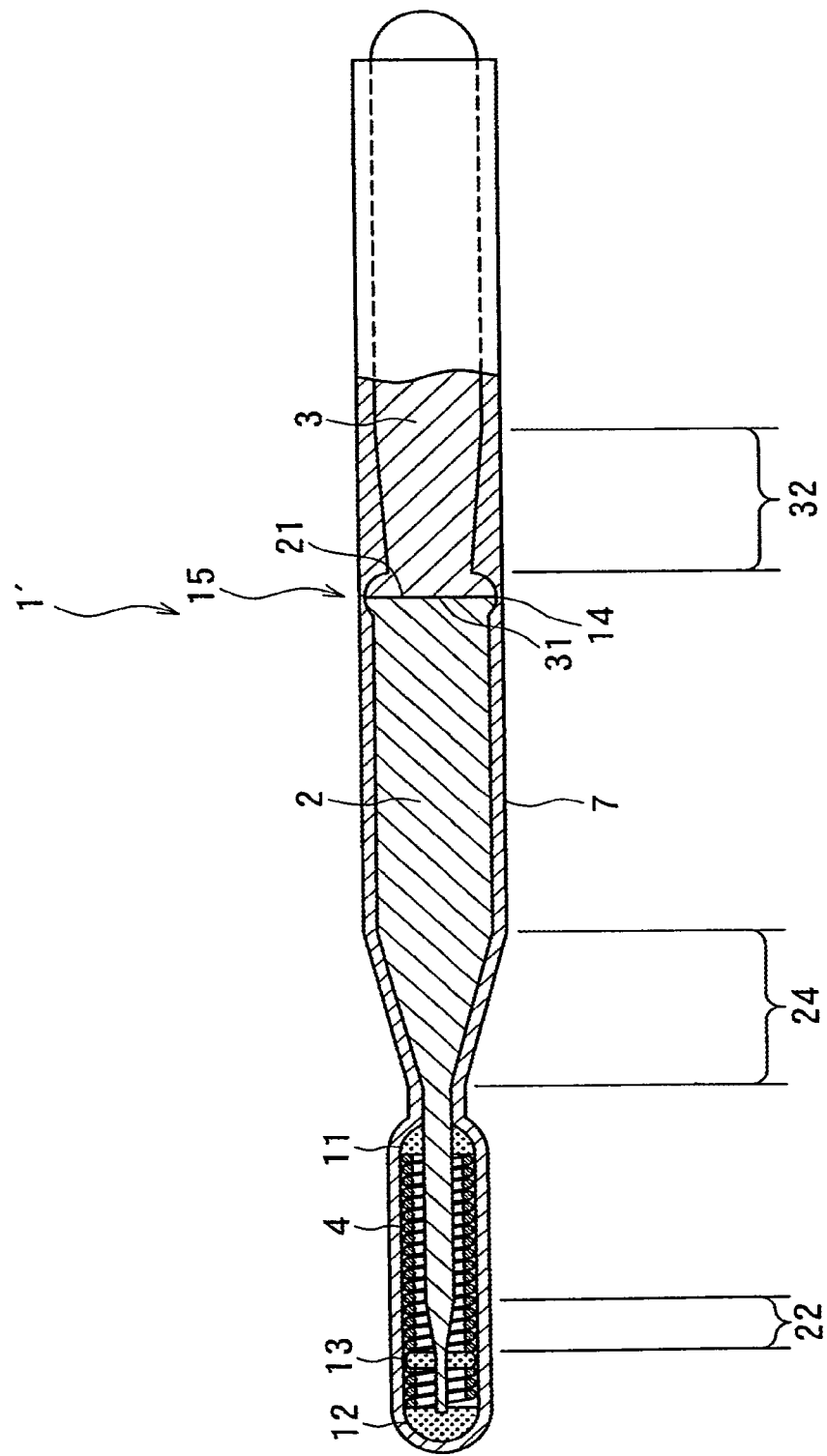

GUIDE WIRE

This application is a continuation of prior application Ser. No. 11/797,328 filed on May 2, 2007, now abandoned, which is a divisional of prior application Ser. No. 10/635,716 filed on Aug. 7, 2003, now abandoned, which claims the benefit of Japanese Patent Application No. 2002-232164 filed on Aug. 8, 2002, Japanese Patent Application No. 2002-355908 filed on Dec. 6, 2002 and Japanese Patent Application No. 2003-156011 filed on May 30, 2003. The entire content of the prior applications is hereby incorporated by reference here in its entirety.

BACKGROUND OF THE INVENTION

1. Field of the Invention

The present invention relates to a guide wire, particularly to a guide wire used to guide a catheter in a body lumen such as a blood vessel.

2. Description of the Related Art

Guide wires are used to guide a catheter in treatment of sites at which open surgeries are difficult or which require minimally invasiveness to the body, for example, PTCA (Percutaneous Transluminal Coronary Angioplasty), or in examination such as cardio-angiography. A guide wire used in the PTCA procedure is inserted, with the distal end projecting from the distal end of a balloon catheter, into the vicinity of a target angiostenosis portion together with the balloon catheter, and is operated to guide the distal end portion of the balloon catheter to the target angiostenosis portion.

A guide wire used to insert a catheter into a blood vessel complicatedly bent requires appropriate flexibility and restoring performance against bending, pushability and torque transmission performance (generically called "operationality") for transmitting an operational force from the proximal end portion to the distal side, and kink resistance (often called "resistance against sharp bending"). To obtain appropriate flexibility as one of the above-described performances, there has been known a guide wire configured such that a metal coil having flexibility is provided around a small-sized core member at the distal end of the guide wire, or a guide wire including a core member made from a superelastic material such as an Ni—Ti alloy for improving the flexibility and restoring performance.

Conventional guide wires include a core member that is substantially made from a single material. In particular, to enhance the operationality of the guide wire, a material having a relatively high elastic modulus is used as the material of the core member. The guide wire including such a core member, however, has an inconvenience that the distal end portion of the guide wire becomes lower in flexibility. On the other hand, if a material having a relatively low elastic modulus is used as the material of the core member for increasing the flexibility of the distal end portion of the guide wire, the operationality of the proximal end portion of the guide wire is degraded. In this way, it has been regarded as difficult to satisfy both requirements associated with the flexibility and operationality by using a core member made from a single material.

A guide wire intended to solve such a problem has been disclosed, for example, in U.S. Pat. No. 5,171,383, wherein a Ni—Ti alloy wire is used as a core member, and the distal side and the proximal side of the alloy wire are heat-treated under different conditions in order to enhance the flexibility of the distal end portion of the alloy wire while enhancing the rigidity of the proximal side of the alloy wire. Such a guide wire, however, has a problem that the control of the flexibility of the distal end portion by heat-treatment has a limitation. For example, even if it is successful to obtain a sufficient flexibility of the distal end portion of the alloy wire, it may often fail to obtain a sufficient rigidity on the proximal side of the alloy wire.

SUMMARY OF THE INVENTION

An object of the present invention is to provide a guide wire capable of making the change in rigidity smooth in the longitudinal direction of the guide wire, thereby improving the operationality and kink resistance of the guide wire.

To achieve the above object, according to a first aspect of the present invention, there is provided a guide wire including a first wire disposed on the distal side of the guide wire, and a second wire disposed on the proximal side from the first wire, the second wire being made from a material having an elastic modulus larger than that of the first wire, wherein the first wire and second wire are joined to each other by welding, and the second wire has, in the vicinity of a welded portion between the first wire and the second wire, a small cross-sectional area portion having a cross-sectional area smaller than a cross-sectional area of a proximal end portion of the first wire.

According to a second aspect of the present invention, there is provided a guide wire including a first wire disposed on the distal side of the guide wire, and a second wire disposed on the proximal side from the first wire, the second wire having a rigidity higher than a rigidity of the first wire, wherein the first wire and the second wire are joined to each other by welding, and a welded portion formed by welding has a projection projecting in the outer peripheral direction, and the second wire has, in the vicinity of a welded portion between the first wire and the second wire, a small cross-sectional area portion having a cross-sectional area smaller than a cross-sectional area of a proximal end portion of the first wire.

Each of the guide wires according to the first and second aspects of the present invention may be further configured as follows.

The guide wire preferably includes a cover layer disposed over at least the welded portion.

The small cross-sectional area portion preferably has an outer diameter smaller than an outer diameter of the proximal end portion of the first wire.

The small cross-sectional area portion preferably includes a portion having a cross-sectional area gradually reduced in the direction toward the distal end of the guide wire.

The small cross-sectional area portion preferably includes a portion having an outer-diameter gradually reduced in the direction toward the distal end of the guide wire.

The small cross-sectional area portion preferably includes a first portion having an outer diameter gradually reduced in the direction toward the distal end of the guide wire, and a second portion having an outer diameter gradually increased in the direction toward the distal end of the guide wire, the second portion being disposed on the distal side from the first portion.

The small cross-sectional area portion preferably has a third portion having a nearly constant outer diameter, the third portion being disposed between the first portion and the second portion.

The first portion preferably has a length in a range of 0.1 to 1,000 times a length of the second portion.

A flexural rigidity of the distal end of the second wire is preferably nearly equal to a flexural rigidity of the proximal end of the first wire.

The guide wire preferably further includes a step filling member for filling a stepped portion formed on the outer periphery of the welded portion.

An outer peripheral surface of a boundary portion between the first portion and the second portion may form a continuous curved plane without any stepped portion.

Each of an outer peripheral surface of a boundary portion between the first portion and the third portion and an outer peripheral surface of a boundary portion between the third portion and the second portion may form a continuous curved plane without any stepped portion.

The first wire may be made from a superelastic alloy.

The second wire may be made from a stainless steel.

The second wire may be made from a Co-based alloy.

The Co-based alloy may be a Co—Ni—Cr alloy.

Each of a connection end face of the first wire to the second wire and a connection end face of the second wire to the first wire may be nearly perpendicular to the axial direction of the first and second wires.

The guide wire may further include a spiral coil covering at least a distal end portion of the first wire.

The welded portion may be located on the proximal side from the proximal end of the coil.

The first wire and the second wire may be welded to each other by a butt resistance welding process.

The guide wire may be used in such a manner that the welded portion be located in a living body.

As described above, since the guide wire of the present invention has the first wire disposed on the distal side and the second wire disposed on the proximal side from the first wire and made from a material having an elastic modulus larger than that of the first wire, it is possible to ensure a high rigidity at a proximal end portion while keeping a high flexibility at a distal end portion, and hence to enhance the pushability, torque transmission performance, and trackability of the guide wire.

Since the first wire and the second wire are joined to each other by welding, it is possible to enhance the joining strength of the joining portion (welded portion), and hence to certainly transmit a torsional torque or pushing force from the second wire to the first wire.

Since the small cross-sectional area portion is provided on the second wire, it is possible to make the change in rigidity of the welded portion and its neighborhood smooth in the longitudinal direction, and hence to certainly prevent kink (sharp bending) or torsion of a portion in the vicinity of the welded portion.

Since the shape of the small cross-sectional area portion is contrived, for example, in such a manner that the small cross-sectional area portion is divided into two parts (first and second portions) or three parts (first, second, and third portions), it is possible to enhance the welding strength of the welded portion, and to relieve or disconcentrate local stress concentration at the small cross-sectional area portion and hence to more certainly prevent kink and torsion.

Accordingly, the present invention can provide a guide wire excellent in operationality, kink resistance, and torsion resistance.

With the configuration that the projection is formed on the welded portion, it is possible to further enhance the joining strength of the joining portion (welded portion) and hence to more certainly transmit a torsional torque or pushing force from the second wire to the first wire.

With the configuration that the cover layer is made from a material capable of reducing the friction of the cover layer, it is possible to improve the sliding resistance of the guide wire in a catheter and hence to further enhance the operationality of the guide wire. Since the sliding resistance of the guide wire is reduced, it is possible to more certainly prevent kink (sharp bending) and torsion of the guide wire, particularly, in the vicinity of the welded portion.

By changing materials used for the cover layer at respective portions, it is possible to enhance the sliding resistance at each of the portions and hence to expand the versability for an operator.

BRIEF DESCRIPTION OF THE DRAWINGS

These and other objects, features, and advantages of the present invention will become more apparent from the following detailed description in conjunction with the accompanying drawings, wherein:

FIGS. 2A to 2C are views showing steps of a procedure for connecting a first wire and a second wire of the guide wire shown in FIG. 1;

FIG. 7 is a longitudinal sectional view showing a second embodiment of the guide wire of the present invention.

DETAILED DESCRIPTION OF THE PREFERRED EMBODIMENTS

A guide wire of the present invention will now be described in detail by way of preferred embodiments shown in the accompanying drawings.

Figure 1:
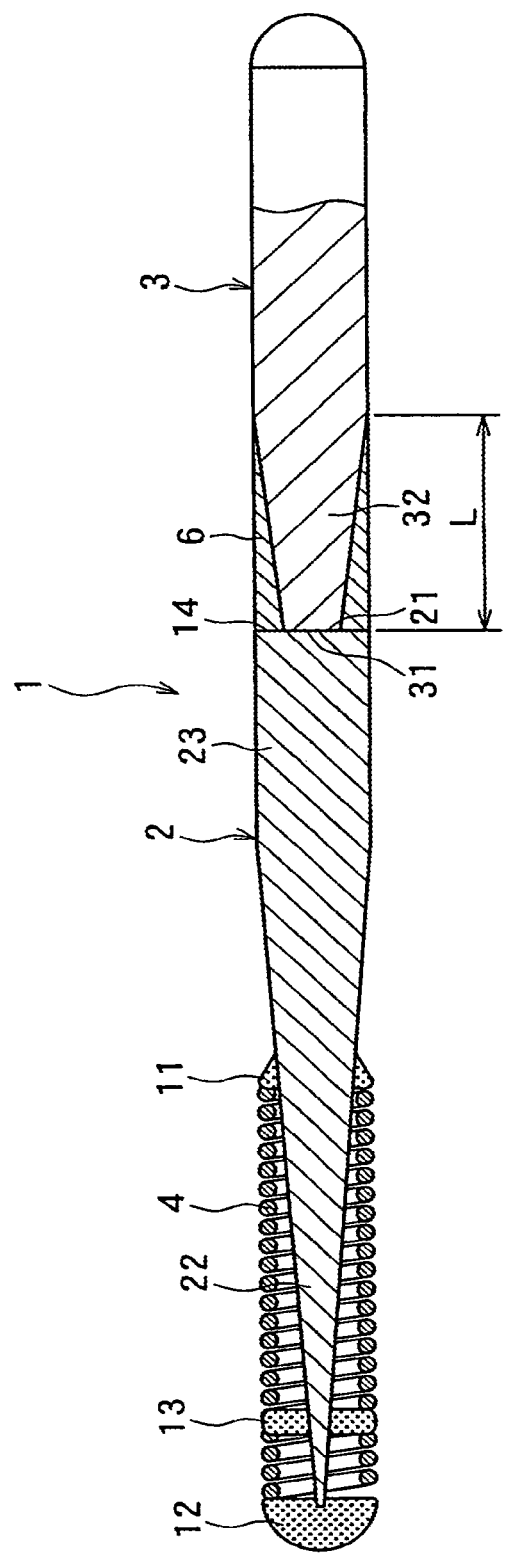
FIG. 1 is a longitudinal sectional view showing a first embodiment of a guide wire of the present invention.

FIG. 1 is a longitudinal sectional view of a first embodiment of a guide wire of the present invention, and FIGS. 2A to 2C are views showing a procedure for joining a first wire and a second wire of the guide wire shown in FIG. 1 to each other. For convenience of description, the right side in FIG. 1 is taken as the "proximal side" and the left side in FIG. 1 is taken as the "distal side". It is to be noted that in FIG. 1 (and in FIGS. 5 to 7 to be described later), for easy understanding, the dimension of the guide wire in the thickness direction is exaggeratedly enlarged while the dimension of the guide wire in the length direction is shortened, and therefore, the ratio of the thickness to the length is significantly different from the actual ratio.

A guide wire 1 shown in FIG. 1, which is of a type used to be inserted in a catheter, includes a first wire 2 disposed on the distal side, a second wire 3 disposed on the proximal side from the first wire 2, and a spiral coil 4. The entire length of the guide wire 1 is not particularly limited but is preferably in a range of about 200 to 5,000 mm. The outer diameter of the guide wire 1 is not particularly limited but is preferably in a range of about 0.2 to 1.2 mm.

The first wire 2 is configured as a wire member having elasticity. The length of the first wire 2 is not particularly limited but is preferably in a range of about 20 to 1,000 mm.

According to this embodiment, the first wire 2 has, at its distal end portion, an outer-diameter gradually reducing portion 22 with its outer diameter gradually reduced in the direction toward the distal end. In the outer-diameter gradually reducing portion 22 of the first wire 2, therefore, the rigidity (flexural rigidity, torsional rigidity) is gradually reduced in the direction toward the distal end. As a result, it is possible to enhance the flexibility of the distal end portion of the guide wire 1, and hence to improve the follow-up performance and safety to a blood vessel and also to prevent sharp-bending and the like.

In the configuration shown in the figure, the first wire 2 has, nearly over the entire length, a taper shape in which the outer diameter is continuously, gradually reduced in the direction toward the distal end. The taper angle of the taper portion of the first wire 2 may be kept constant or changed along the longitudinal direction.

According to this embodiment, the outer-diameter gradually reducing portion 22 is tapered such that the outer diameter is continuously reduced with a nearly constant reduction ratio in the direction toward the distal end. In other words, the taper angle of the outer-diameter gradually reducing portion 22 is kept nearly constant along the longitudinal direction. In the outer-diameter gradually reducing portion 22, therefore, the change in rigidity becomes more moderate (or smooth) along the longitudinal direction. Unlike such a configuration, the reduction ratio of the outer diameter of the outer-diameter gradually reducing portion 22 (taper angle of the outer-diameter gradually reducing portion 22) may be changed along the longitudinal direction. For example, portions in each of which the reduction ratio of the outer diameter is relatively large and portions in each of which the reduction ratio of the outer diameter is relatively small may be alternately repeated by a plurality of numbers. In this case, the outer-diameter gradually reducing portion 22 may have a portion in which the reduction ratio of the outer diameter in the direction toward the distal end becomes zero.

The outer diameter of a proximal end portion of the first wire 2 is kept nearly constant along the longitudinal direction. Unlike the configuration shown in the figure, the outer diameter of nearly the whole of the first wire 2 may be gradually reduced in the direction toward the distal end. In other words, nearly the whole of the first wire 2 may be composed of the outer-diameter gradually reducing portion 22.

The material for forming the first wire 2 is not particularly limited but may be selected from metal materials such as stainless steels. In particular, alloys having pseudo-elasticity (for example, superelastic alloys) are preferable, and superelastic alloys are more preferable. Superelastic alloys are relatively flexible, good in restoring performance, and less susceptible to reforming. Accordingly, if the first wire 2 is made from a superelastic alloy, the guide wire 1 including such a first wire 2 has, at its distal portion, a high flexibility and a high restoring performance against bending, and a high trackability to a blood vessel complicatedly curved or bent, to thereby enhance the operationality of the guide wire 1. Even if the first wire 2 is repeatedly deformed, that is, curved or bent, the first wire 2 is no or less plastic deforming because of its high restoring performance. This prevents degradation of the operationality due to the plastic deforming of the first wire 2 during use of the guide wire 1.

Pseudo-elastic alloys include those of a type in which the stress-strain curve in a tensile test has any shape, those of a type in which a transformation point such as As, Af, Ms, or Mf can be significantly measured or not measured, and those of all types in which the shape is greatly deformed by stress and then restored nearly to an original shape by removal of stress.

Examples of superelastic alloys include Ni—Ti alloys such as an Ni—Ti alloy containing Ni in an amount of 49-52 atomic %, a Cu—Zn alloy containing Zn in an amount of 38.5 to 41.5 wt %, a Cu—Zn—X alloy containing X in an amount of 1 to 10 wt % (X: at least one kind selected from a group consisting of Be, Si, Sn, Al, and Ga), and an Ni—Al alloy containing Al in an amount of 36 to 38 atomic %. Of these materials, the Ni—Ti alloy is preferable.

The distal end of the second wire 3 is joined to the proximal end of the first wire 2. The second wire 3 is a wire member having elasticity. The length of the second wire 3 is not particularly limited but may be in a range of about 20 to 4,800 mm.

The second wire 3 is made from a material having an elastic modulus (Young's modulus or modulus of longitudinal elasticity, modulus of rigidity or modulus of transverse elasticity, or bulk modulus) larger than that of the first wire 2. The second wire 3 can thus exhibit an appropriate rigidity (flexural rigidity, torsional rigidity). As a result, the guide wire 1 becomes firm, to improve the pushability and torque transmission performance, thereby enhancing the operationality at the time of insertion of the guide wire 1.

The material for forming the second wire 3 is not particularly limited but may be selected from metal materials, for example, stainless steels (all kinds specified in SUS, for example, SUS304, SUS303, SUS316, SUS316L, SUS316J1, SUS316J1L, SUS405, SUS430, SUS434, SUS444, SUS429, SUS430F, and SUS302), piano wire steels, cobalt alloys, and alloys having pseudo-elasticity.

In particular, cobalt alloys are preferably used for the second wire 3. This is because the second wire 3 made from a cobalt alloy has a high elastic modulus and an appropriate elastic limit. Such a second wire 3 exhibits a good torque transmission performance, thereby hardly causing a problem associated with buckling or the like. Any type of cobalt alloy may be used insofar as it contains cobalt. In particular, a cobalt alloy containing cobalt as a main component (that is, a cobalt-based alloy containing cobalt in an amount [in wt %] being the largest among the contents of all components of the alloy) is preferably used, and further, a Co—Ni—Cr alloy is more preferable. The use of the cobalt alloy having such a composition as the material for forming the second wire 3 is effective to further enhance the above-described effects. The cobalt alloy having such a composition is also advantageous in that since the alloy exhibits plasticity in deformation at room temperature, the second wire 3 made from such a cobalt alloy is easily deformable into a desired shape, for example, during use of the guide wire. A further advantage of the cobalt alloy having such a composition is as follows: namely, since the second wire 3 made from such a cobalt alloy has a high elastic modulus and is cold-formable even if it exhibits a high elastic limit, the second wire 3 can be thinned while sufficiently preventing occurrence of buckling, and therefore, can exhibit a high flexibility and a high rigidity enough to be inserted into a desired site.

The Co—Ni—Cr alloy is exemplified by an alloy containing 28-50 wt % of Co, 10-30 wt % of Ni, and 10-30 wt % of Cr, the balance being Fe. In this alloy, part of any component may be substituted by another element (substitution element). The incorporation of such a substitution element exhibits an effect inherent to the kind thereof. For example, the incorporation of at least one kind selected from a group consisting of Ti, Nb, Ta, Be, and Mo further improves the strength of the second wire 3. In the case of incorporating one or more substitution elements other than Co, Ni, and Cr, the total content of the substitution elements is preferably in a range of 30 wt % or less.

For example, part of Ni may be substituted by Mn, which is effective to further improve the workability. Part of Cr may be substituted by Mo and/or W, which is effective to further improve the elastic limit. Of the Co—Ni—Cr alloys, a Co—Ni—Cr—Mo alloy is particularly preferable.

Examples of compositions of the Co—Ni—Cr alloys include (1) 40 wt % Co-22 wt % Ni-25 wt % Cr-2 wt % Mn-0.17 wt % C-0.03 wt % Be—Fe(balance), (2) 40 wt % Co-15 wt % Ni-20 wt % Cr-2 wt % Mn-7 wt % Mo-0.15 wt % C-0.03 wt % Be—Fe(balance), (3) 42 wt % Co-13 wt % Ni-20 wt % Cr-1.6 wt % Mn-2 wt % Mo-2.8 wt % W-0.2 wt % C-0.04 wt % Be—Fe(balance), (4) 45 wt % Co-21 wt % Ni-18 wt % Cr-1 wt % Mn-4 wt % Mo-1 wt % Ti-0.02 wt % C-0.3 wt % Be—Fe(balance), and (5) 34 wt % Co-21 wt % Ni-14 wt % Cr-0.5 wt % Mn-6 wt % Mo-2.5 wt % Nb-0.5 wt % Ta—Fe(balance). The wording "Co—Ni—Cr alloy" used herein is the conception including these Co—Ni—Cr alloys.

If a stainless steel is used as the material for forming the second wire 3, the pushability and torque transmission performance of the guide wire 1 can be further enhanced.

The first wire 2 and the second wire 3 may be made from different alloys, and particularly, the first wire 2 is preferably made from a material having an elastic modulus smaller than that of the material of the second wire 3. With this configuration, the distal end portion of the guide wire 1 has a high flexibility, and the proximal end portion of the guide wire 1 has a high rigidity (flexural rigidity, torsional rigidity). As a result, the guide wire 1 has a high pushability and a high torque transmission performance, thereby enhancing the operationality, and also exhibits, on the distal side, a high flexibility and a high restoring performance, thereby improving trackability and safety to a blood vessel.

As one preferred combination of materials of the first wire 2 and the second wire 3, the first wire 2 is made from a superelastic alloy and the second wire 3 is made from a Co—Ni—Cr alloy or a stainless steel. With this configuration, the above-described effects become more significant.

From the viewpoint of enhancing the flexibility and restoring performance of the distal end portion of the first wire 2, it is preferred to use a Ni—Ti alloy as the superelastic alloy for forming the first wire 2.

The coil 4 is a member formed by spirally winding a wire, particularly a fine wire, and is provided so as to cover the distal end portion of the first wire 2. In the configuration shown in FIG. 1, the distal end portion of the first wire 2 is disposed in an approximately axially center portion of the coil 4 in such a manner as to be not in contact with the inner surface of the coil 4. It is to be noted that in the configuration shown in FIG. 1, the coil 4 is loosely disposed in such a manner that a slight gap remains between adjacent spirally wound wire portions in a state that no external force is applied to the coil 4; however, the coil 4 may be tightly disposed in such a manner that no gap remains between the adjacent spirally wound wire portions in a state that no external force is applied to the coil 4.

The coil 4 may be made from a metal material such as a stainless steel, a superelastic alloy, a cobalt alloy, a noble metal such as gold, platinum, or tungsten, or an alloy containing such a noble metal. In particular, the coil 4 is preferably made from a radiopaque material such as a noble metal. If the coil 4 is made from such a radiopaque material, the guide wire 1 can exhibit an X-ray contrast performance. This makes it possible to insert the guide wire 1 in a living body while confirming the position of the distal end portion of the guide wire 1 under fluoroscopy. The distal side and proximal side of the coil 4 may be made from different alloys. For example, the distal side of the coil 4 may be formed of a coil made from a radiopaque material and the proximal side of the coil 4 be formed of a coil made from a relatively radiolucent material such as a stainless material. The entire length of the coil 4 is not particularly limited but may be in a range of about 5 to 500 mm.

The proximal end portion and the distal end portion of the coil 4 are fixed to the first wire 2 by a fixing material 11 and a fixing material 12, respectively, and an intermediate portion (close to the distal end) of the coil 4 is fixed to the first wire 2 by a fixing material 13. Each of the fixing materials 11, 12, and 13 is a solder (brazing material). Alternatively, each of the fixing materials 11, 12, and 13 may be an adhesive. In addition, in place of using the fixing material, the coil 4 may be fixed to the first wire 2 by welding. To prevent damage of the inner wall of a blood vessel, the leading end surface of the fixing material 12 is preferably rounded.

According to this embodiment, since the first wire 2 is partially covered with the coil 4, the contact area of the first wire 2 with the inner wall of a catheter used together with the guide wire 1 is small, with a result that it is possible to reduce the sliding resistance of the guide wire 1 in the catheter. This is effective to further improve the operationality of the guide wire 1.

In this embodiment, the wire having a circular shape in cross-section is used for the coil 4; however, the cross-sectional shape of the wire used for the coil 4 may be another shape such as an elliptic shape or a quadrilateral shape (especially, rectangular shape).

In the guide wire 1, the first wire 2 and the second wire 3 are joined to each other by welding. A welded portion (joining portion) 14 between the first wire 2 and the second wire 3 has a high joining strength, thereby allowing the guide wire 1 to certainly transmit a torsional torque or pushing force from the second wire 3 to the first wire 2.

In this embodiment, a connection end face 21 of the first wire 2 to the second wire 3 and a connection end face 31 of the second wire 3 to the first wire 2 are each formed into a plane nearly perpendicular to the axial (longitudinal) direction of both the wires 2 and 3. This significantly facilitates working for forming the connection end faces 21 and 31, to achieve the above-described effects without complicating the steps for producing the guide wire 1.

It is to be noted that each of the connection end faces 21 and 31 may be tilted relative to the plane perpendicular to the axial (longitudinal) direction of both the wires 2 and 3, or formed into a recessed or raised shape.

The method of welding the first wire 2 and the second wire 3 to each other is not particularly limited but is generally exemplified by spot welding using laser or butt resistance welding such as butt seam welding. In particular, to ensure a high joining strength of the welded portion, butt resistance welding is preferable.

The second wire 3 of the guide wire 1 has, in the vicinity of the welded portion 14, a small cross-sectional area 32 with its cross-sectional area being smaller than that of a proximal end portion 23 of the first wire 2. In other words, in a portion from the connection end face 31 to a specific position on the proximal side, that is, in the small cross-sectional area portion 32, the cross-sectional area of the second wire 3 is smaller than that of the proximal end portion 23 of the first wire 2. In this embodiment, the outer diameter of the small cross-sectional area portion 32 is smaller than that of the proximal end portion 23 of the first wire 2, and therefore, the cross-sectional area of the small cross-sectional area portion 32 is smaller than that of the proximal end portion 23. In other words, the area of the connection end face 31 is smaller than that of the connection end face 21.

Since the second wire 3 is made from a material having an elastic modulus larger than that of the first wire 2 as described above, if the outer diameter of the distal end portion of the second wire 3 is the same as that of the proximal end portion 23 of the first wire 2, the rigidity (flexural rigidity, torsional rigidity) of the guide wire 1 is rapidly changed between both sides of the welded portion 14. On the contrary, according to the present invention, the small cross-sectional area portion 32 is provided at the distal end portion of the second wire 3, and the rigidity (flexural rigidity, torsional rigidity) of the small cross-sectional area portion 32 is made small. Accordingly, the change in rigidity (flexural rigidity, torsional rigidity) of the welded portion 14 and its neighborhood becomes moderate (smooth) along the longitudinal direction, to thereby enhance the operationality of the guide wire 1.

According to this embodiment, the small cross-sectional area portion 32 includes a portion in which the outer diameter is gradually reduced in the direction toward the distal end, that is, the cross-sectional area is gradually reduced in the direction toward the distal end. Accordingly, the rigidity (flexural rigidity, torsional rigidity) of the small cross-sectional area portion 32 is gradually reduced from the proximal end to the distal end thereof, that is, in the direction toward the distal end of the guide wire 1, to thereby make the change in rigidity (flexural rigidity, torsional rigidity) of the guide wire 1 more moderate (smooth) along the longitudinal direction.

In the configuration shown in the figure, the small cross-sectional area portion 32 has, over the entire length, the taper shape with its outer diameter gradually reduced in the direction toward the distal end; however, the small cross-sectional area portion 32 may have a portion having a constant outer diameter (cross-sectional area), for example, on the distal end side, and may further have, on the distal side from the outer-diameter constant portion, a portion with its outer diameter gradually increased in the direction toward the welded portion 14. Even in this case, the same effect as that described above can be obtained. It is to be noted that modifications of the small cross-sectional area portion 32 will be fully described in detail.

The length of the small cross-sectional area portion 32 (denoted by character L in FIG. 1) is not particularly limited but is preferably in a range of about 3 to 1,000 mm, more preferably, about 3 to 300 mm. If the length L is within the above range, the change in rigidity (flexural rigidity, torsional rigidity) of the welded portion 14 and its neighborhood can be made more moderate (smooth) along the longitudinal direction.

In the small cross-sectional area portion 32, the flexural rigidity of the distal end (connection end face 31) of the second wire 3 is preferably nearly equal to the flexural rigidity of the proximal end (connection end face 21) of the first wire 2. With this configuration, the change in rigidity of the welded portion 14 and its neighborhood can be made more moderate (smooth) along the longitudinal direction. In addition, letting the geometrical moment of inertia (determined only by the shape and dimension of the connection end face 31) of the connection end face 31 be $I_2$ and the Young's modulus of the material of the second wire 3 be $E_2$, the flexural rigidity of the distal end of the second wire 3 is expressed by $E_2 \cdot I_2$. On the other hand, letting the geometrical moment of inertia (determined only by the shape and dimension of the connection end face 21) of the connection end face 21 be $I_1$ and the Young's modulus of the material of the first wire 2 be $E_1$, the flexural rigidity of the distal end of the first wire 2 is expressed by $E_1 \cdot I_1$.

The guide wire 1 in this embodiment has a step filling member 6 for filling a stepped portion formed on the outer periphery of the welded portion 14. The stepped portion, which is formed on the outer periphery of the welded portion 14 due to the fact that the outer diameter of the distal end of the second wire 3 is smaller than that of the proximal end of the first wire 2, is filled with the step filling member 6, to thereby prevent the reduction in sliding performance of the guide wire 1 due to the presence of the stepped portion.

In the configuration shown in the figure, the step filling member 6 covers the small cross-sectional area portion 32. The outer diameter of the member 6 is kept nearly constant along the longitudinal direction, and the inner diameter of the member 6 is gradually reduced in the direction toward the distal end. As a result, the outer diameter of a portion, including the welded portion 14 and the small cross-sectional area portion 32, of the guide wire 1 is kept nearly constant along the longitudinal direction. This is effective to more certainly eliminate adverse effect of the stepped portion exerted on the sliding performance of the guide wire 1.

The material for forming the step filling member 6 is not particularly limited, and may be generally selected from resin materials and metal materials. To reduce adverse effect of the member 6 exerted on the rigidity of the guide wire 1, the member 6 is preferably made from a relative soft material such as solder, plastic, or wax. The shape of the step filling member 6 is not limited to that shown in the figure but may be any shape such as a coil shape.

In this embodiment, the welded portion 14 is located on the proximal side from the proximal end of the coil 4, but the welded portion 14 may be located on the distal side from the proximal end of the coil 4.

If the rigidity of the first wire 2 is smaller than that of the second wire 3, the size of the connection end face 31 may be larger than that of the connection end face 21.

Figure 5:
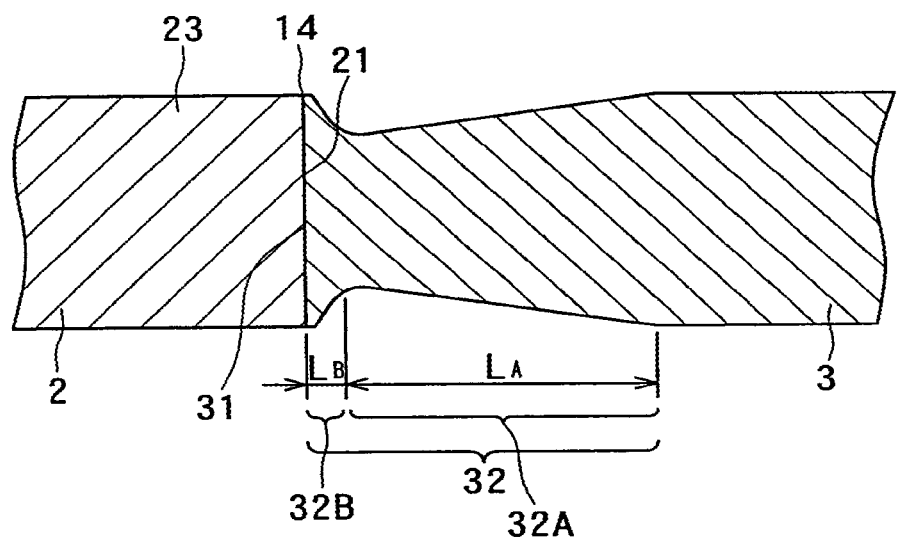
FIG. 5 is a longitudinal sectional view showing a modification of a small cross-sectional area portion of the guide wire of the present invention.
Figure 6:
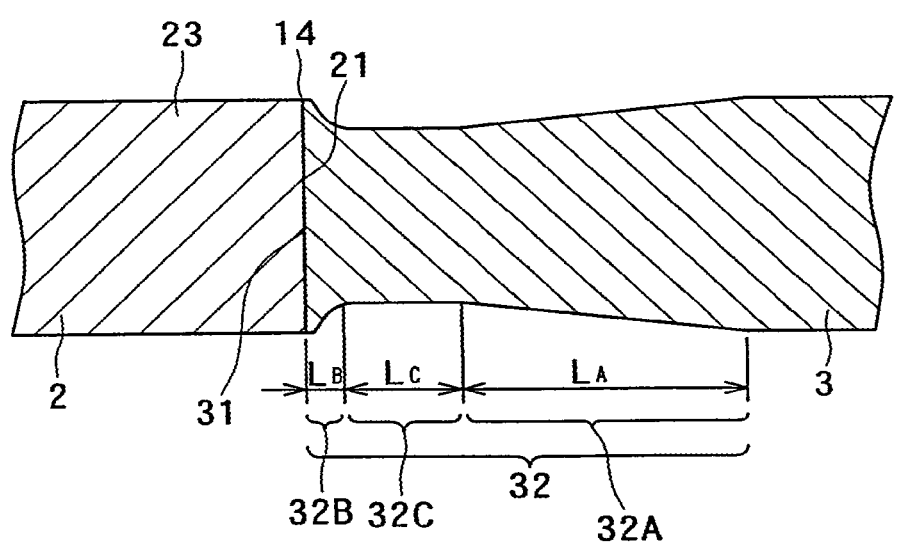
FIG. 6 is a longitudinal sectional view showing another modification of a small cross-sectional area portion of the guide wire of the present invention.

FIGS. 5 and 6 are longitudinal sectional views showing modifications of the small cross-sectional area portion of the guide wire of the present invention.

A small cross-sectional area portion 32 according to a modification shown in FIG. 5 has a first portion 32A with its outer diameter gradually reduced in the direction toward the distal end, and a second portion 32B with its outer diameter gradually increased in the direction toward the distal end, wherein the second portion 32B is disposed on the distal side from the first portion 32A. The outer peripheral surface of a boundary portion between the first portion 32A and the second portion 32B has a continuous curved plane without substantial stepped portion (smooth plane). With this configuration, it is possible to prevent or relieve stress concentration at the boundary portion, and hence to more certainly prevent torsion or kink, that is, to improve the kink resistance.

The maximum outer diameter of the second portion 32B is located at a connection end face 31 (the distal end of a second wire 3), and is nearly equal to the outer diameter of a connection end face 21 (the proximal end of a first wire 2). Accordingly, as compared with the configuration shown in FIG. 1, the small cross-sectional area portion 32 shown in FIG. 5 is advantageous in enlarging the area of a welded surface of a welded portion 14, thereby improving the welding strength. As a result, when a torsional torque or pushing force is applied from the second wire 3 to the first wire 2, it is possible to more certainly prevent breakage of the welded portion 14 due to stress concentration at the welded portion 14 or lacking of the welding strength of the welded portion 14.

In the small cross-sectional area portion 32, letting the length of the first portion 32A be $L_A$ and the length of the second portion 32B be $L_B$, the length $L_A$ is longer than the length $L_B$. In other words, the taper angle of the first portion 32A is smaller than that of the second portion 32B.

The length $L_A$ of the first portion 32A is preferably in a range of about 0.1 to 1,000 times, more preferably, 1.0 to 1,000 times, most preferably, 1.0 to 50 times the length $L_B$ of the second portion 32B. With this configuration, it is possible to suppress stress concentration at the welded portion 14, and hence to realize smooth transition of rigidity.

A small cross-sectional area portion 32 according to another modification shown in FIG. 6 has a third portion 32C located between a first portion 32A and a second portion 32B. The third portion 32C has a nearly constant outer diameter, which may be smaller than each of the outer diameters of the first portion 32A and the second portion 32B. In other words, the third portion 32C is preferably the minimum outer-diameter portion of the small cross-sectional area portion 32. Other configurations of this modification are the same as those of the previous modification shown in FIG. 5.

The small cross-sectional area portion 32 shown in FIG. 6 has not only the same function and effect as those of the small cross-sectional area portion 32 shown in FIG. 5, but also the following additional function and effect: namely, since the minimum outer-diameter portion of the small cross-sectional area portion 32 may be taken as the third portion 32C continuously extending for a specific length (denoted by character $L_C$), it is possible to more certainly relieve stress concentration at the minimum outer-diameter portion of the small cross-sectional portion 32 as compared with the configuration shown in FIG. 5. As a result, when a torsional torque or pushing force is applied from the second wire 3 to the first wire 2, it is possible to more certainly prevent torsion, kink, breakage, and the like of the minimum outer-diameter portion of the small cross-sectional area portion 32.

The third portion 32C preferably has rigidity nearly equal to that of a portion in the vicinity of the proximal end portion 23 of the first wire 2. Since the outer diameter of the third portion 32C is set such that the rigidity of the third portion 32C is nearly equal to the portion in the vicinity of the proximal end portion 23 of the first wire 2, it is possible to realize smooth transition of rigidity from the small cross-sectional area portion 32 to the proximal end portion 23 of the first wire 2.

Each of the outer peripheral surface of a boundary portion between the first portion 32A and the third portion 32C and the outer peripheral surface of a boundary portion between the third portion 32C and the second portion 32B forms a continuously curved plane without substantial stepped portion (smooth plane). With this configuration, the above-described effect of preventing or relieving stress concentration at the boundary portion can be obtained.

The relationship among a length $L_A$ of the first portion 32A, a length $L_B$ of the second portion 32B, and a length $L_C$ of the third portion 32C is not particularly limited but is preferably set to a relationship of $L_B \leq L_C \leq L_A$ or $L_B \leq L_A \leq L_C$, more preferably $L_B < L_C \leq L_A$.

In this embodiment, the length $L_A$ of the first portion 32A is preferably in a range of about 0.1 to 1,000 times, more preferably, 0.1 to 10 times the length $L_B$ of the second portion 32B. With this configuration, it is possible to suppress stress concentration at the welded portion 14, and hence to realize smooth transition of rigidity.

To sufficiently obtain an effect of relieving stress concentration at the minimum outer-diameter portion while keeping the strength of the small cross-sectional area portion 32, the length $L_C$ of the third portion 32C is preferably in a range of about 0.1 to 200 mm, more preferably, about 1 to 50 mm.

The outer periphery of the small cross-sectional area portion 32 shown in each of FIGS. 5 and 6 may be covered with the above-described step filling member 6. With this configuration, the above-described effect of eliminating the degradation of the sliding performance of the guide wire 1 due to the presence of the stepped portion can be obtained.

The procedure of joining the first wire 2 and the second wire 3 to each other by butt seam welding as one example of butt resistance welding will be described with reference to FIGS. 2A to 2C. FIGS. 2A to 2C show steps 1 to 3 of the procedure of joining the first wire 2 and the second wire 3 to each other by butt seam welding.

In the step 1, the first wire 2 and the second wire 3 are fixed (mounted) to a butt welder (not shown).

In the step 2, the connection end face 21 on the proximal side of the first wire 2 and the connection end face 31 on the distal side of the second wire 3 are butted to each other while a specific voltage is applied thereto by the butt welder. With this operation, a fused layer (welded surface) is formed at the contact portion, whereby the first wire 2 and the second wire 3 are strongly joined to each other.

In the step 3, a projection at the joining portion (welded portion 14), which is formed by deformation upon butt resistance welding, is removed. A portion, on the proximal side from the welded portion 14, of the second wire 3, that is, the distal end portion of the second wire 3 is ground, to form the small cross-sectional area portion 32 having a desired shape as shown in FIG. 1, 5, or 6, that is, the small cross-sectional area portion 32 with its outer diameter gradually reduced in the direction toward the distal end.

Alternatively, the small cross-sectional area portion 32 having a desired shape (with its outer diameter gradually reduced in the direction toward the distal end) may be previously prepared by grinding the distal end portion of the second wire 3, and then welded to the first wire 2 by the butt resistance welding process.

Figure 3:
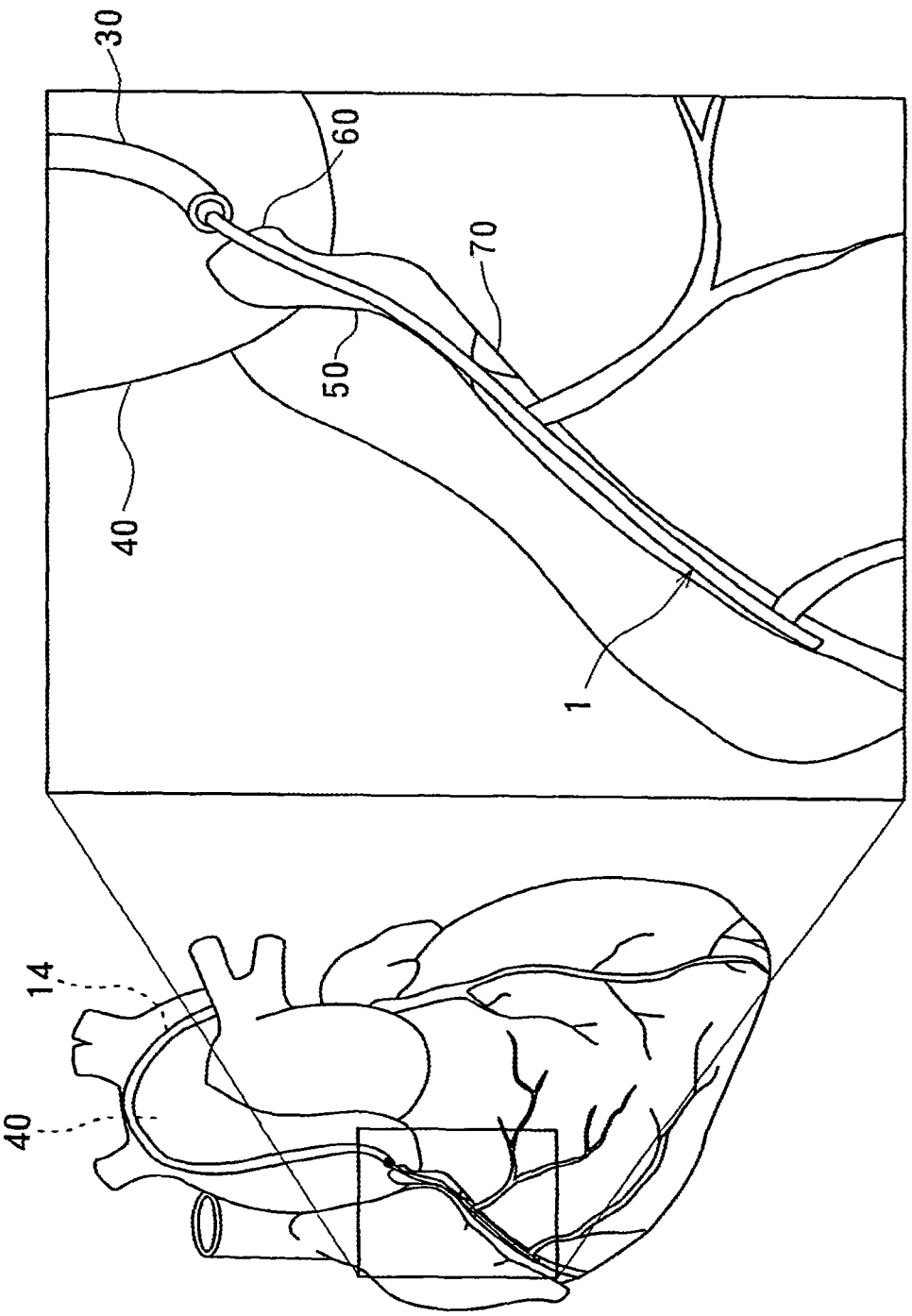
FIG. 3 is a typical view illustrating an example of how to use the guide wire of the present invention.
Figure 4:
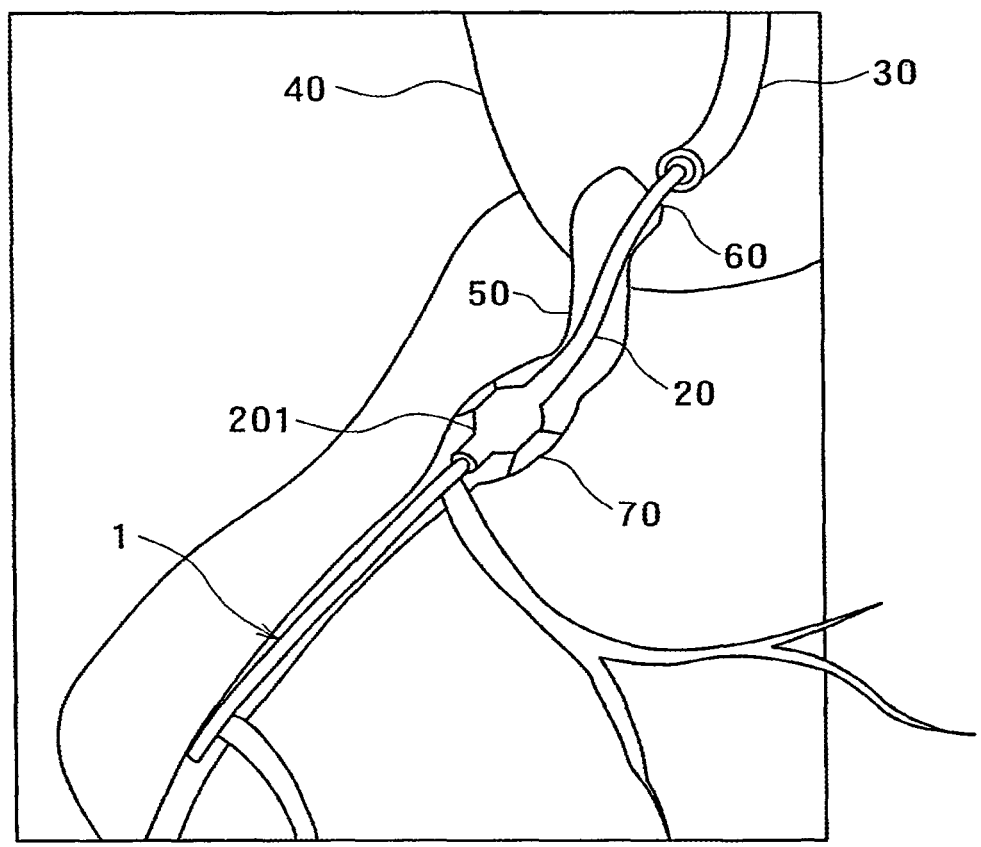
FIG. 4 is a typical view illustrating the example of how to use the guide wire of the present invention.

FIGS. 3 and 4 are views showing the operational state of the guide wire 1 of the present invention during use in the PTCA process.

In FIGS. 3 and 4, reference numeral 40 denotes an aortic arch, 50 is a right coronary artery of a heart, 60 is an ostium of the right coronary artery 50, and 70 is a target angiostenosis portion. Further, reference numeral 30 denotes a guiding catheter for certainly guiding the guide wire 1 from an arteria fermoralis into the right coronary artery 50, and 20 is a balloon catheter having at its distal end an expandable and contractible balloon 201 for dilating the target angiostenosis portion 70.

As shown in FIG. 3, the guide wire 1 is moved in such a manner that the distal end thereof projecting from the distal end of the guiding catheter 30 is inserted in the right coronary artery 50 through the ostium 60 of the right coronary artery 50. The guide wire 1 is further advanced, and is stopped when the distal end thereof passes the target angiostenosis portion 70 in the right coronary artery 50. In this state, an advance path of the balloon catheter 20 is ensured. At this time, the welded portion 14 of the guide wire 1 is located in the living body, more specifically, in the vicinity of the distal portion of the aortic arch 40.

As shown in FIG. 4, the balloon catheter 20 is inserted around the guide wire 1 from the proximal side of the guide wire 1. The balloon catheter 20 is then advanced in such a manner that the distal end thereof projects from the distal end of the guiding catheter 30, goes ahead along the guide wire 1, and enters the right coronary artery 50 from the ostium 60 of the right coronary artery 50. The balloon catheter 20 is stopped when the balloon 201 reaches a position corresponding to that of the target angiostenosis portion 70.

A fluid for inflating the balloon 201 is injected in the balloon catheter 20 from the proximal side of the balloon catheter 20, to inflate the balloon 201, thereby dilating the target angiostenosis portion 70. As a result, deposits such as cholesterol adhering on the arterial wall of the target angiostenosis portion 70 are physically compressed against the arterial wall, to eliminate blocking of blood flow.

FIG. 7 is a longitudinal sectional view showing a second embodiment of the guide wire of the present invention. The second embodiment of the guide wire of the present invention will now be described with reference to FIG. 7, principally, about differences from the previous embodiment, with the description of the same features omitted.

According to a guide wire 1' in this embodiment, a first wire 2 has an outer-diameter gradually reducing portion 22 and an outer-diameter gradually reducing portion 24 provided on the proximal side from the outer-diameter gradually reducing portion 22. In this way, the first wire 2 may have outer-diameter gradually reducing portions at a plurality of positions.

In this embodiment, a welded portion 14 has a projection 15 projecting in the outer peripheral direction. The formation of such a projection 15 is effective to enlarge a joining area between the first wire 2 and the second wire 3, and hence to significantly enhance the joining strength. This is advantageous in more certainly transmitting a torsional torque or pushing force from the second wire 3 to the first wire 2.

The formation of the projection 15 may make the welded portion 14 between the first wire 2 and the second wire 3 easily visible under fluoroscopy. As a result, it is possible to easily, certainly recognize the advancing state of the guide wire 1' and a catheter in a blood vessel or the like by checking the fluoroscopic image, and hence to shorten the operation time and to improve the safety.

As described above, the first wire 2 and the second wire 3 are generally made from materials having different elastic moduli. Accordingly, because of provision of the projection 15, an operator can easily, certainly, recognize a portion, at which the elastic modulus is relatively largely changed, of the guide wire 1'. This enhances the operationality of the guide wire 1', to shorten the operation time and improve the safety.

The height of the projection 15, which depends on the outer diameters of the first wire 2 and the second wire 3, is not particularly limited, but is preferably in a range of 0.001 to 0.3 mm, more preferably, 0.005 to 0.05 mm. If the height of the projection 15 is less than the lower limit, it may fail to sufficiently obtain the above-described effects depending on the materials of the first wire 2 and the second wire 3. If the height of the projection 15 is more than the upper limit, since the inner diameter of a lumen, in which the guide wire 1 is to be inserted, of a balloon catheter is fixed, the outer diameter of the second wire 3 on the proximal side must be thin relative to the height of the projection 15, with a result that it may become difficult to ensure sufficient physical properties of the second wire 3.

In the configuration shown in FIG. 7, each of one side (upper side in FIG. 7) and the other side (lower side in FIG. 7) of the projection 15 is formed into an approximately circular-arc shape in longitudinal cross-section, and the welded portion 14 is located on the maximum outer-diameter portion of the projection 15. This is advantageous in enlarging an area of the welded surface of the welded portion 14, thereby obtaining a higher joining strength (welding strength).

According to the present invention, the shape of the projection 15 and the position of the welded portion 14 relative to the projection 15 are not limited to those described above. For example, each of one side and the other side of the projection 15 may be formed into a non-circular (non-circular arc) such as a trapezoidal or triangular shape in longitudinal cross-section. The proximal side and the distal side of the projection 15 may be formed into shapes asymmetric to each other with respect to the welded surface (connection end face 21, 31) of the welded portion 14. The axial position of the welded surface of the welded portion 14 relative to the projection 15 is not necessarily located at the central portion as shown in FIG. 7 but may be located at a position offset to the proximal side (second wire 3 side) or on the distal side (first wire 2 side). With this configuration, it is possible to prevent or relieve stress concentration at the welded portion 14, and hence to more certainly prevent breakage of the welded portion 14 due to stress concentration at the welded portion 14 when a torsional torque or pushing force is applied from the second wire 3 to the first wire 2.

The guide wire 1' has a cover layer 7 on the outer surface (outer peripheral surface) side. In this way, the guide wire of the present invention may be configured to have a cover layer that covers the whole or part of the outer surface (outer peripheral surface). Such the cover layer 7 is formed for satisfying various purposes, one of which is to reduce the friction (sliding friction) of the guide wire 1' for improving the sliding performance of the guide wire 1', thereby enhancing the operationality of the guide wire 1'.

To satisfy the above-described purpose, the cover layer 7 is preferably made from a material capable of reducing the friction of the guide wire 1'. With this configuration, since the friction resistance (sliding resistance) of the guide wire 1' against the inner wall of a catheter used together with the guide wire 1' is reduced, the sliding performance of the guide wire 1' is improved, to enhance the operationality of the guide wire 1' in the catheter. Further, since the sliding resistance of the guide wire 1' is reduced, it is possible to more certainly prevent, at the time of movement and/or rotation of the guide wire 1' in the catheter, kink (sharp bending) or torsion of the guide wire 1', particularly, in the vicinity of a welded portion of the guide wire 1'.

Examples of the materials capable of reducing the friction of the guide wire 1' include polyorefins such as polyethylene and polypropylene, polyvinyl chloride, polyesters (such as PET and PBT), polyamide, polyimide, polyurethane, polystyrene, polycarbonate, silicone resins, fluorocarbon resins (such as PTFE and ETFE), silicone rubbers, various kinds of elastomers (for example, thermoplastic elastomers such as polyamide-based elastomer and polyester-based elastomer), and composite materials thereof. In particular, a fluorocarbon resin or a composite material thereof is preferable, and PTFE is more preferable.

According to this embodiment, a hydrophilic material or a hydrophobic material can be also used as another preferred example of the material capable of reducing the friction of the guide wire 1'. In particular, the hydrophilic material is preferable.

Examples of the hydrophilic materials include a cellulose based polymer, a polyethylene oxide based polymer, a maleic anhydride based polymer (for example, a maleic anhydride copolymer such as methylvinylether-maleic anhydride copolymer), an acrylic amide based polymer (for example, polyacrylic amide or polyglycidyl methacrylate-dimethyl acrylic amide [PGMA-DMAA] block copolymer), water-soluble nylon, polyvinyl alcohol, and polyvinyl pyrolidone.

In many cases, the hydrophilic material can exhibit a lubricating performance in a wet (water-absorbing) state. The use of the cover layer 7 made from such a hydrophilic material is effective to reduce the friction resistance (sliding resistance) of the guide wire 1' against the inner wall of a catheter used together with the guide wire 1', to improve the sliding performance of the guide wire 1', thereby enhancing the operationality of the guide wire 1' in the catheter.

The provision of the cover layer 7 is effective to omit or simplify the above-described step filling member 6. To be more specific, since the cover layer 7 is formed in such a manner as to cover a stepped portion in the vicinity of the welded portion 14, even if the step filling member 6 is omitted or simplified, it is possible to sufficiently prevent degradation of the sliding performance of the guide wire 1' due to the presence of the stepped portion.

The cover layer 7 may be formed in such a manner as to the whole or part of the guide wire 1' in the longitudinal direction; however, the cover layer 7 is preferably formed in such a manner as to cover the welded portion 14, that is, formed at a portion including the welded portion 14.

The cover layer 7 covers the small cross-sectional area portion 32 and the projection 15, and has a substantially uniform outer diameter. The term "substantially uniform outer diameter" used herein contains an outer diameter smoothly changed within such a range as not to cause any inconvenience in use of the guide wire.

The thickness (in average) of the cover layer 7 is not particularly limited but is preferably in a range of about 1 to 20 µm, more preferably, about 2 to 10 µm. If the thickness of the cover layer 7 is less than the lower limit, the effect obtained by formation of the cover layer 7 may be not sufficiently achieved and the cover layer 7 may be often peeled. If the thickness of the cover layer 7 is more than the upper limit, the physical properties of the wire may be obstructed and the cover layer 7 may be often peeled.

According to the present invention, the outer peripheral surface of the guide wire body (including the first wire 2, the second wire 3, and coil 4) may be subjected to a treatment (such as chemical treatment or heat treatment) for improving the adhesion characteristic of the cover layer 7, or may be provided with an intermediate layer for improving the adhesion characteristic of the cover layer 7.

The cover layer 7 may have a nearly constant composition or different compositions at respective portions. For example, the cover layer 7 may have a first region (first cover layer) for covering at least the coil 4 and a second region (second cover layer) on the proximal side from the first region, wherein the first cover layer and the second cover layer be made from different materials. Although the first cover layer and the second layer may be formed so as to be continuous to each other in the longitudinal direction as shown in the figure, the proximal end of the first cover layer may be separated from the distal end of the second cover layer, or the first cover layer may be partially overlapped to the second cover layer.

Figure 8A:
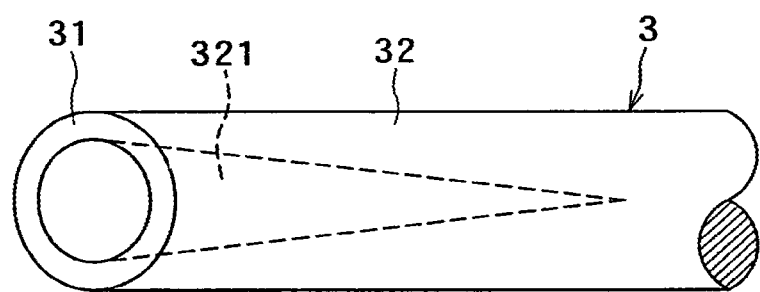
FIGS. 8A and 8B are perspective views showing further modifications of the small cross-sectional area portion of a second wire of the guide wire of the present invention.
Figure 8B:
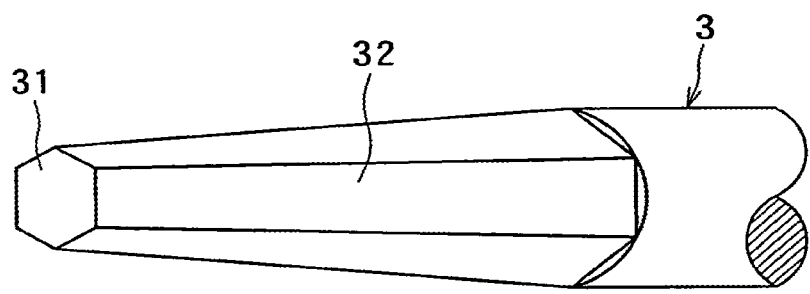

FIGS. 8A and 8B are perspective views showing further modifications of the small cross-sectional area portion of the second wire of the guide wire of the present invention.

A small cross-sectional area portion 32 of a second wire 3 shown in FIG. 8A has an outer diameter, which is kept constant and is equal to that of a portion on the proximal side from the small cross-sectional area portion 32. The small cross-sectional area portion 32 has a hollow portion 321 with its inner diameter gradually increased in the direction toward the distal end. That is to say, the hollow portion 321 is formed into a conical or truncated conical shape. Since such a hollow portion 321 is formed, the cross-sectional area of the small cross-sectional area portion 32 is smaller than that of a proximal end portion 23 of a first wire 2 and is gradually reduced in the direction toward the distal end, with a result that the rigidity (flexural rigidity, torsional rigidity) of the small cross-sectional area portion 32 is gradually reduced in the direction toward the distal end. According to the present invention, such a small cross-sectional area portion 32 having the shape shown in FIG. 8A has the same effect as that obtained in each of the previous embodiments. The small cross-sectional area portion 32, in which the cross-sectional area can be gradually reduced without changing the outer diameter by the presence of the hollow portion 321, has another advantage in eliminating the need of provision of the step filling member 6 because no stepped portion is formed at a welded portion 14 between the proximal portion 23 of the first wire 2 and the small cross-sectional area portion 32. The hollow portion 321 may be formed into a pyramid or truncated pyramid shape. In this case, the welding may be performed in a state that part of the proximal end portion 23 of the first wire 2 is inserted in the hollow portion 321 of the second wire 3. With this configuration, since the change in rigidity becomes smoother between both sides of the welded portion 14, it is possible to further improve the kink resistance.

A small cross-sectional area portion 32 of a second wire 3 shown in FIG. 8B has a truncated pyramid shape, more specifically, a truncated hexagonal pyramid shape, wherein the dimension of the polygonal shape (regular hexagonal shape) in cross-section is gradually reduced in the direction toward the distal end. As a result, the cross-sectional area of the small cross-sectional area portion 32 is gradually reduced in the direction toward the distal end, with a result that the rigidity (flexural rigidity, torsional rigidity) thereof is gradually reduced in the direction toward the distal end. Such a small cross-sectional area portion 32 shown in FIG. 8B has the same effect as that obtained in each of the previous embodiments.

In the above-described embodiments, each of the composing elements of the guide wire may be replaced with a composing element having any other configuration exhibiting the similar effect, and may be provided with any other additional element.

While the preferred embodiments of the present invention have been described using specific terms, such description is for illustrative purposes only, and it is to be understood that changes and variations may be made without departing from the spirit or scope of the following claims.

What is claimed is:

1. A guide wire comprising:
    a first wire disposed on a distal side of said guide wire; and
    a second wire disposed on a proximal side from said first wire;
    wherein said first wire and said second wire are joined to each other by welding;
    said second wire has a first portion having an outer diameter smoothly reduced in a direction toward a distal end of the second wire, and has a second portion having an outer diameter smoothly increased in the direction toward the distal end of the second wire, wherein the second portion is disposed on the distal side from the first portion and extends to the distal end of the second wire,
    the second wire has a third portion having a substantially constant outer diameter, said third portion being disposed between said first portion and said second portion of the second wire, and
    the third portion has a rigidity substantially equal to that of a proximal end portion of the first wire.

2. The guide wire according to claim 1, wherein said first portion of said second wire has a length in a range of 0.1 to 1,000 times a length of said second portion.

3. The guide wire according to claim 1, wherein the first wire possesses a proximal end face, and the outer diameter of the entirety of the first wire other than the proximal end face is not greater than the outer diameter of the proximal end face of the first wire.

4. The guide wire according to claim 1, wherein the second wire possesses a distal end face, and the outer diameter of the entirety of the second wire other than the distal end face is not greater than the outer diameter of the distal end face of the second wire.

5. The guide wire according to claim 1, wherein the first wire possesses a proximal end face, a constant-diameter portion, and a tapered portion having an outer diameter which decreases toward a distal side of the first wire.

6. The guide wire according to claim 5, wherein the tapered portion of the first wire is formed on the distal side of the first wire, and the constant-diameter portion of the first wire is formed on a proximal side of the first wire, and wherein the constant-diameter portion extends from the proximal end face of the first wire to the tapered portion of the first wire and has a greater outer diameter than that of the entirety of the first wire other than at the constant-diameter portion.

7. The guide wire according to claim 1, wherein the first portion, the second portion, and the third portion are covered by a step filling member.

\* \* \* \* \*